United States Patent [19]

Koszyk et al.

[11] Patent Number: 5,342,951
[45] Date of Patent: Aug. 30, 1994

[54] 2- AND 3-SULFUR DERIVATIVES OF 1,5-IMINOSUGARS

[75] Inventors: Francis J. Koszyk, Prospect Heights; Richard A. Mueller, Glencoe, both of Ill.

[73] Assignee: G.D. Searle & Co., Skokie, Ill.

[21] Appl. No.: 100,788

[22] Filed: Aug. 2, 1993

Related U.S. Application Data

[60] Division of Ser. No. 942,572, Sep. 9, 1992, Pat. No. 5,268,482, and a continuation-in-part of Ser. No. 861,696, Apr. 1, 1992, Pat. No. 5,206,251.

[51] Int. Cl.$^5$ .................. C07D 211/54; C07D 211/42; C07D 211/44; C07D 211/46
[52] U.S. Cl. .................. 546/217; 546/220; 546/242; 546/219
[58] Field of Search ............... 546/217, 243, 219, 220, 546/242

[56] References Cited

U.S. PATENT DOCUMENTS

| | | | |
|---|---|---|---|
| 2,812,330 | 11/1957 | Dodson | 546/219 |
| 4,182,763 | 1/1980 | Casten et al. | 424/251 |
| 4,182,767 | 1/1980 | Murai | 546/242 |
| 4,533,668 | 8/1985 | Matsumura et al. | 514/321 |
| 4,639,436 | 1/1987 | Junge et al. | 514/24 |
| 4,849,430 | 7/1989 | Fleet et al. | 514/315 |
| 4,871,747 | 10/1989 | Kinast et al. | 514/315 |
| 4,957,926 | 9/1990 | Jacob et al. | 514/315 |
| 5,003,072 | 3/1991 | Partis | 546/243 |
| 5,011,829 | 4/1991 | Hirsch et al. | 514/50 |
| 5,025,021 | 6/1991 | Getman et al. | 514/302 |
| 5,026,713 | 6/1991 | Getman et al. | 514/302 |
| 5,030,638 | 7/1991 | Partis et al. | 514/315 |
| 5,128,347 | 7/1992 | Getman | 546/219 |

FOREIGN PATENT DOCUMENTS

| | | |
|---|---|---|
| 298350 | 1/1989 | Fed. Rep. of Germany . |
| 8703903 | 7/1987 | PCT Int'l Appl. . |

OTHER PUBLICATIONS

Fleet, Chem. Lett. 7, 1051–1054 (1986).
Kiso, J. Carbohydr. Chem. 10, 25–45 (1991).
Frank et al., Antimicrobial Agents an Chemotherapy, 1369–1374 (1987).

*Primary Examiner*—C. Warren Ivy
*Assistant Examiner*—D. Margaret M. Mach
*Attorney, Agent, or Firm*—Scott J. Meyer

[57] ABSTRACT

Novel derivatives of 1-deoxynojirimycin are disclosed which have thio or sulfinyl substituents at C-2 or C-3. These compounds are useful inhibitors of lentiviruses such as visna virus and human immunodeficiency virus. Methods of chemical synthesis of these derivatives and intermediates therefor are also disclosed.

2 Claims, No Drawings

2- AND 3-SULFUR DERIVATIVES OF 1,5-IMINOSUGARS

CROSS-REFERENCE TO RELATED APPLICATION

This is a division of application Ser. No. 07/942,572, filed Sep. 3, 1992 now U.S. Pat. No. 5,268,482, and this is a continuation-in-part of copending application Ser. No. 07/861,696, filed Apr. 1, 1992 now U.S. Pat. No. 5,206,251.

BACKGROUND OF THE INVENTION

This invention relates to novel derivatives of 1,5-dideoxy-1,5-imino-D-glucitol having thio or sulfinyl substituents at C-2 and/or C-3, and, more particularly, to the chemical synthesis of these derivatives and intermediates therefor. These compounds are useful for inhibiting glycosidase enzymes and for inhibiting viruses such as lentiviruses.

1,5-dideoxy-1,5-imino-D-glucitol (deoxynojirimycin or DNJ) and its N-alkyl and O-acylated derivatives are known inhibitors of glycosidase enzymes and also inhibitors of viruses such as human immunodeficiency virus (HIV). See, e.g., U.S. Pat. Nos. 4,849,430; 5,003,072; 5,030,638 and PCT Int'l. Appln. WO 87/03903. Several of these derivatives also are effective against other viruses such as HSV and CMV as disclosed in U.S. Pat. No. 4,957,926. In some cases antiviral activity is enhanced by combination of the DNJ derivative with other antiviral agents such as AZT as described in U.S. Pat. No. 5,011,829. Various of these DNJ derivative compounds are antihyperglycemic agents based on their activity as glycosidase inhibitors. See, e.g., U.S. Pat. Nos. 4,182,763, 4,533,668 and 4,639,436. The 2-acetamide derivatives of DNJ also are reported to be potent glycosidase inhibitors by Fleet et al., Chem. Lett. 7, 1051–1054 (1986); and Kiso et al. J. Carbohydr. Chem. 10, 25–45 (1991).

Notwithstanding the foregoing, the search continues for the discovery and novel synthesis of new and improved antiviral compounds.

BRIEF DESCRIPTION OF THE INVENTION

In accordance with the present invention, novel derivatives of 1,5-dideoxy-1,5-imino-D-glucitol having thio or sulfinyl substituents at C-2 and/or C-3 are provided. These novel DNJ derivative compounds and various of their intermediates are useful inhibitors of glycosidase enzymes and also have useful antiviral activity as demonstrated against lentivirus. Compounds of this invention are also useful intermediates for the synthesis of antiviral compounds. According to another embodiment of the invention, novel methods of chemical synthesis of these compounds and their intermediates are provided.

The novel C-2 and/or C-3 thio or sulfinyl substituted derivatives of 1,5-dideoxy-1,5-imino-D-glucitol can be represented by the following general structural Formulas I and II.

The compounds of Formula I are in the gluco stereochemical configuration whereas those of Formula II are in the altro stereochemical configuration.

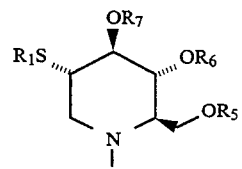

I

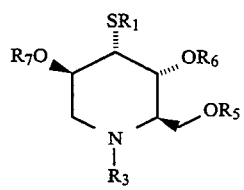

II

In Formulas I and II, $R_1$ is a $C_1$–$C_6$ alkyl group, arylalkyl group, aryl, substituted aryl, substituted arylalkyl; $R_3$ is H or a $C_1$–$C_8$ branched or unbranched alkyl group, alkoxyalkyl, alkenyl, alkynyl, arylalkyl, substituted arylalkyl, or acyl such as alkylacyl, alkenylacyl, alkynylacyl, arylacyl, substituted arylacyl, arylalkylacyl, substituted arylalkylacyl, carbonyl; and $R_5$, $R_6$ and $R_7$ are independently H or $COR_2$ where $R_2$=alkyl having $C_1$–$C_6$ branched or unbranched alkyl groups, aryl, or alkylaryl.

Preferred compounds of Formula I are the following:

2-Sulfur Derivatives of DNJ 1,5-Dideoxy-1,5-imino-2-S-methyl-4,6-O-(R-phenylmethylene)-2-thio-D-glucitol 1,5-Dideoxy-1,5-imino-2-S-methyl-2-thio-D-glucitol 1,5-Dideoxy-1,5-[[(2-methoxyethoxy)carbonyl]imino]-2-S-phenyl-4,6-O-(R-phenylmethylene)-2-thio-D-glucitol 1,5-Dideoxy-1,5-imino-2-S-phenyl-4,6-O-(R-phenylmethylene)-2-thio-D-glucitol 1,5-Dideoxy-1,5-imino-2-S-phenyl-2-thio-D-glucitol 1,5-(Butylimino)-1,5-dideoxy-2-S-methyl-2-thio-D-glucitol, triacetate 1,5-(Butylimino)-1,5-dideoxy-2-S-methyl-2-sulfinyl-D-glucitol Preferred compounds of Formula II are the following:

3-Sulfur Derivatives of DNJ 1,5-Dideoxy-1,5-imino-3-S-methyl-3-thio-D-altritol 1,5-Dideoxy-1,5-imino-3-S-phenyl-3-thio-D-altritol 1,5-(Butylimino)-1,5-dideoxy-3-S-methyl-3-thio-D-altritol The novel synthesis of compounds of Formulas I and II comprises the formation of structural modifications at C2 and C3 of DNJ and the nucleophilic opening of N-carboalkoxy-2,3-anhydro-DNJ.

The starting N-carboalkoxy-2,3-anhydro-DNJ can be chemically synthesized by the four reaction steps shown in the following Reaction Schemes A(1) and A(2) as described in co-pending application Ser. No. 07/861,696, filed Apr. 1, 1992.

Scheme A(1): Generic Synthesis of N-carboalkoxy-2,3-anhydro-DNJ

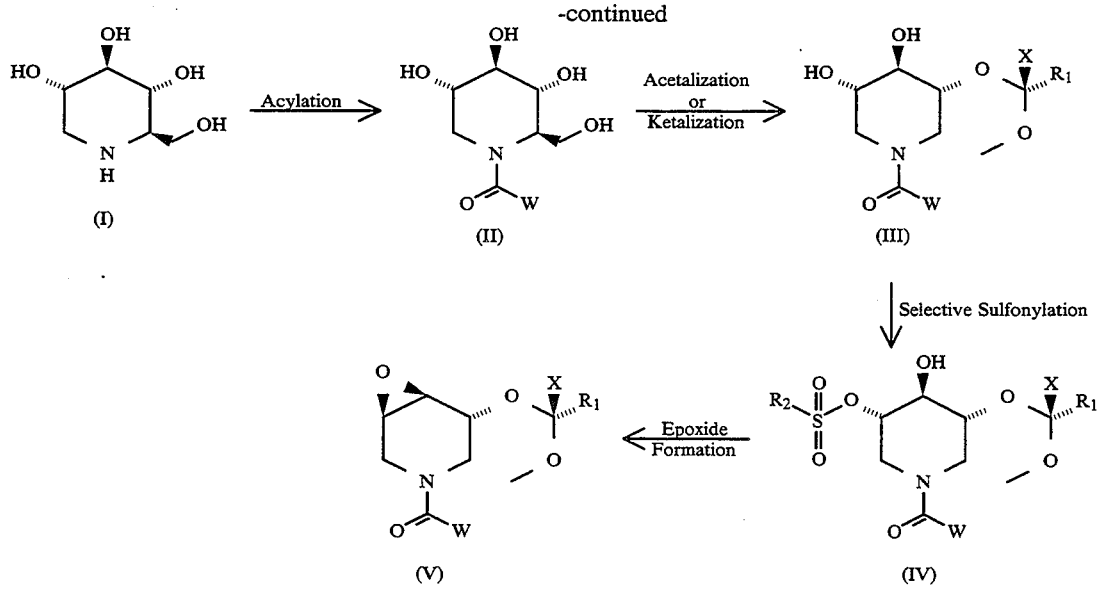

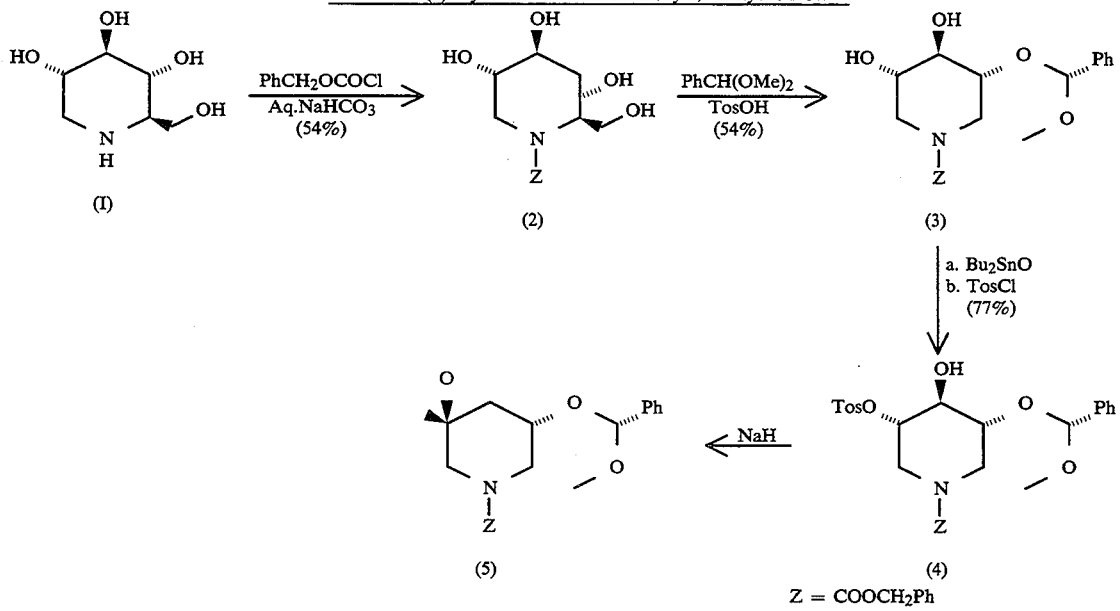

Scheme A(2): Synthesis of N-carboalkoxy-2,3-anhydro-DNJ

Z = COOCH₂Ph

The foregoing Reaction Scheme A comprises the following general reaction steps:

(a) The starting material, DNJ (I), is N-acylated with an acylating agent to form a carbamate derivative of DNJ (II);

(b) The hydroxyls at C-4 and C-6 are protected with a hydroxyl protecting agent by acetalization or ketalization to form an acetal or ketal (III);

(c) The hydroxyl at C-2 is protected by regioselective sulfonylation with a sulfonylating agent at C-2 to give the 2-sulfonated intermediate (IV);

(d) A 2,3-anhydro derivative is formed by epoxidation at C-2 and C-3 to give the epoxide intermediate (V).

N-Acylation of DNJ (I) in step (a) can be carried out by conventional N-acylation procedures well known to those skilled in the art. Suitable general procedures for acylation of amines are described in U.S. Pat. No. 5,003,072; March, J. in *Advanced Organic Chemistry*, Wiley, New York, 1985; Patai, S. (Ed.) in *The Chemistry of Amides*, Wiley, New York, 1970. For example, DNJ is N-acylated to form carbamate or thiocarbamate using a variety of reagents such as chloroformates (e.g., methyl chloroformate, ethyl chloroformate, vinyl chloroformate, benzyl chloroformate) or dicarbonates (e.g., di-tertbutyl dicarbonate). The reaction of DNJ (I) with anhydrides, chloroformates or dicarbonates is preferentially carried out by dissolving in one or more of polar, protic or dipolar aprotic solvents (such as water, methanol, ethanol, dimethylformamide, dimethylacetamide, N-methylpyrrolidone, or dimethyl sulfoxide) and in the presence of a base (e.g, potassium carbonate, lithium carbonate, sodium carbonate, cesium carbonate, triethylamine, pyridine, 4-dimethylaminopyridine, diisopropylethylamine, 1,8-diazabicyclo[5,4,0]undec-7-ene). N-Acylation is preferentially carried out by reacting DNJ (I) with alkyl or aryl chloroformate in solvents such as DMF or aqueous sodium bicarbonate at 20°–50° C. to give the product (II).

Protection of the hydroxyl groups at C-4 and C-6 in step (b) to give acetal or ketal derivative (III) can be carried out by conventional hydroxyl protection procedures such as those described, e.g., in U.S. Pat. No. 5,003,072 and in Greene, T. W., and Wuts, P. G. M., *Protective Groups in Organic Synthesis,* Wiley, New York, 1991. The cyclic acetals and ketals are formed by the reaction of 4,6-dihydroxy compound (II) with an aldehyde or a ketone in the presence of an acid catalyst. Illustrative carbonyl (or carbonyl equivalents such as dimethyl acetal or dimethyl ketal) compounds useful in this reaction are acetone, acetaldehyde, methyl phenyl ketone, benzaldehyde, 4-methoxybenzaldehyde, 2,4-dimethoxybenzaldehyde, 4-dimethylaminobenzaldehyde, 2-nitrobenzaldehyde, 2,2,2-trichloroacetaldehyde (chloral) and acetophenone. The acid catalysts suitable for this reaction are, e.g., para-toluene sulfonic acid, cat. HCl, cat. sulfuric acid, $FeCl_3$, $ZnCl_2$, $SnCl_2$ and $BF_3$-ether, and the reaction is carried out in the presence of aprotic solvents such as methylene chloride, 1,2-dimethoxyethane, dioxane, dimethylformamide, dimethylacetamide or dimethylsulfoxide. Thus paratoluene sulfonic acid is added to a solution of benzaldehyde dimethyl acetal in organic medium, e.g., dimethylformamide, and reacted with N-acyl-DNJ (II) at 20°-65° C. to give the product (III).

The selective protection of the hydroxy group at C-2 in compound (III) in step (c) can be carried out by regioselective sulfonylation to give the sulfonate (IV). For example, compound (III) is conveniently refluxed with dibutyltinoxide in solvents (such as benzene, toluene, xylene, methanol or ethanol and the like) to form a homogeneous solution. The stannylene intermediate is then reacted with p-toluenesulfonyl chloride to give tosylate (IV). Other sulfonyl chlorides such as benzenesulfonyl chloride, 4-bromobenzenesulfonyl chloride, 4-nitrobenzenesulfonyl chloride, methanesulfonyl chloride, 2,6-dimethylbenzenesulfonyl chloride, 1-naphthylenesulfonyl chloride, and 2-naphthylenesulfonyl chloride can also be used in this reaction.

The epoxide intermediate (V) is readily prepared in step (d) by treatment of the sulfonate (IV) with base such as sodium hydride, potassium hydride, lithium hydride, cesium carbonate, potassium carbonate and potassium tert-butoxide using aprotic or dipolar aprotic solvents such as dimethylformamide, dimethylacetamide, dimethylsulfoxide, dimethoxyethane, tetrahydrofuran, dioxane, diethyl ether, dibutyl ether and tert-butyl methyl ether.

In accordance with a preferred embodiment of the invention, the compounds of Formulas I and II can be chemically synthesized by the sequence of reactions shown in the following generic Sulfur Reaction Schemes B, C and D in which, illustratively, $R_1$, $R_2$, $R_3$ and $R_4$ are independently $C_1$–$C_4$ alkyl groups or phenyl, $R_5$ is $OR_6$ and $R_6$ is $CH_2CH_2OCH_3$, W is $OCH_2Ph$ or OMe, X is H and V is $OC(CH_3)_3$. Alternatively, V in Reaction Scheme B can be, e.g., any of the following: carbamate such as t-butyloxycarbonyl, 9-fluorenyloxycarbonyl, benzhydryloxycarbonyl, cyclopentyloxycarbonyl, cyclohexyloxycarbonyl, piperidinoxycarbonyl; acyl such as formyl, acetyl, propionyl, butyryl, isobutyryl, s-butyryl, phenylacetyl, chloroacetyl, and acetoacetyl; trifluoroacetyl; or aryl-or alkylsulfonyl such as p-toluenesulfonyl.

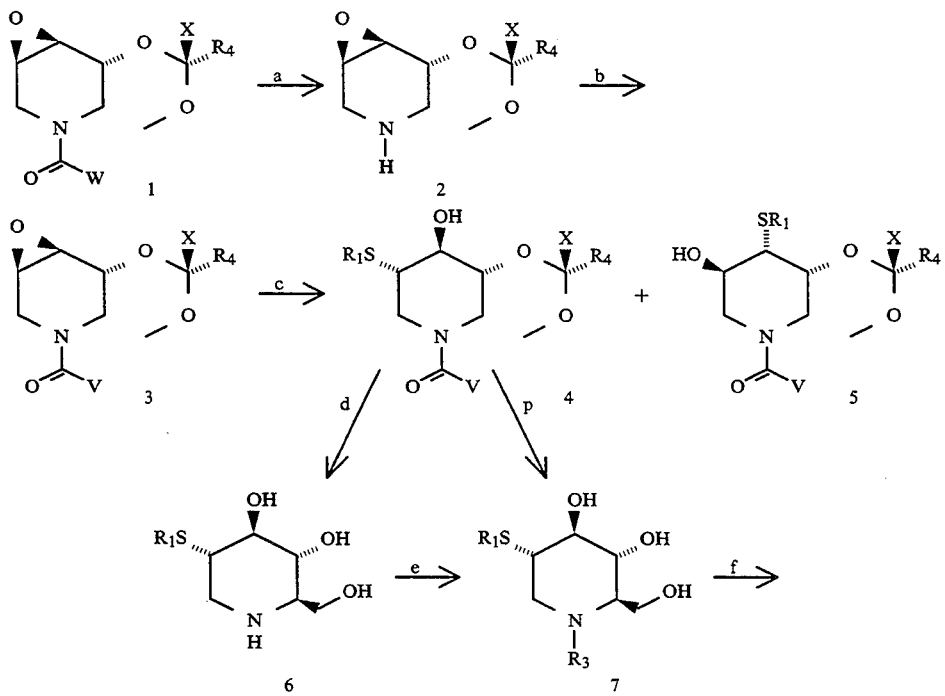

Scheme B: Synthesis of 2- and 3-Thia Substituted 1,5-Iminosugars

-continued
Scheme B: Synthesis of 2- and 3-Thia Substituted 1,5-Iminosugars
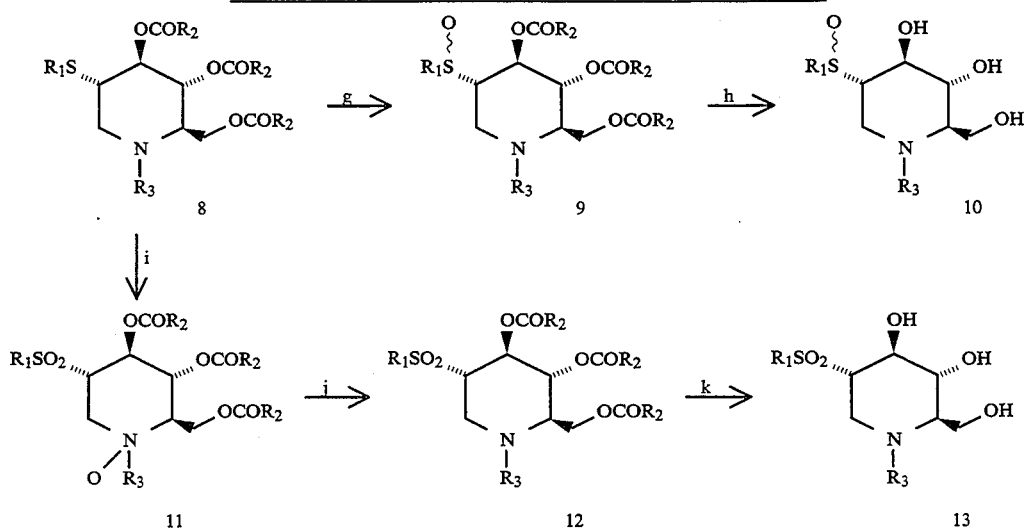
Scheme C: Synthesis of 2- and 3-Thia Substituted 1,5-Iminosugars
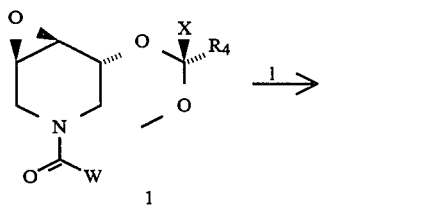
1
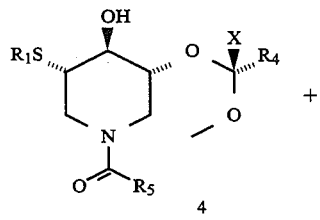
4
+
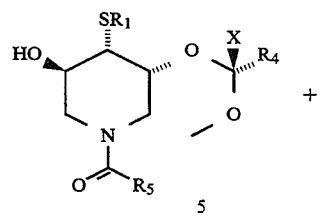
5
+
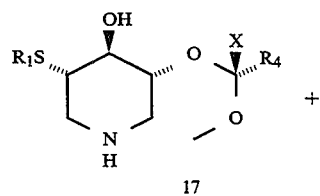
17
+
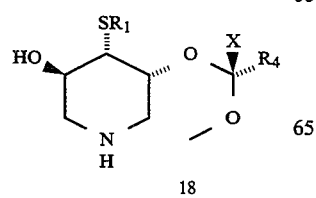
18
-continued
Scheme C: Synthesis of 2- and 3-Thia Substituted 1,5-Iminosugars
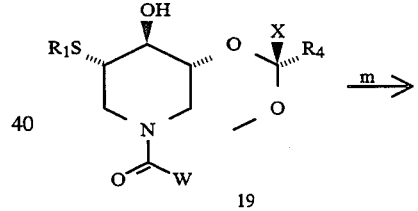
19
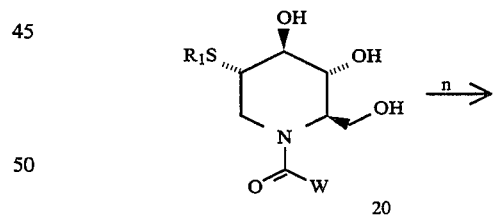
20
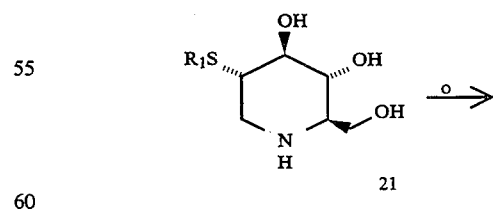
21
22

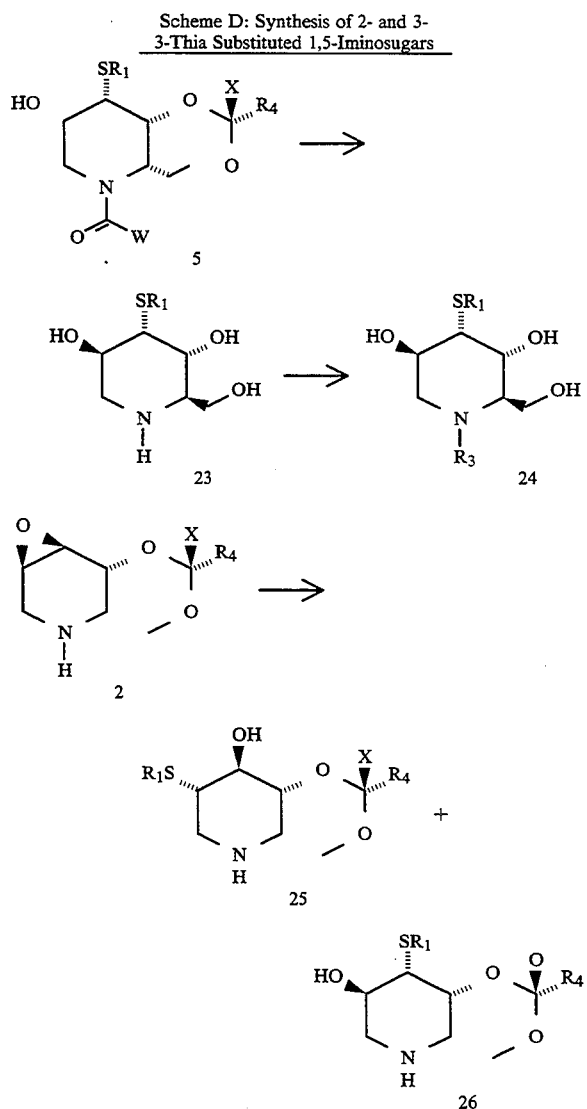

Scheme D: Synthesis of 2- and 3-3-Thia Substituted 1,5-Iminosugars

ILLUSTRATIVE REACTION CONDITIONS

Illustrative reaction conditions for carrying out the synthesis steps of Reaction Schemes B–D are as follows:

A nitrogen acyl group in compound 1 can be removed in step a by base hydrolysis at a temperature of from about 40° to 100° C. to give the novel compound 2. Illustrative bases suitable for this reaction are aqueous sodium hydroxide, lithium hydroxide or potassium hydroxide with or without the presence of organic solvents such as methanol, ethanol, ethylene glycol, acetonitrile and dioxane. The carbamates can also be cleaved by other reagents such as sulfur nucleophiles (e.g., sodium thiomethoxide and lithium thiopropoxide), iodotrimethylsilane, lithium peroxide, or hydrazine. Benzyl or substituted benzyl carbamates can be removed by base hydrolysis as described above or by catalytic hydrogenation in an atmosphere of hydrogen in the presence of a noble metal catalyst such as palladium or platinum at a pressure of from one to 50 atmospheres, in a single or mixed solvent(s) such as ethanol, ethyl acetate, toluene, or tetrahydrofuran, or by hydrogenation in an inert atmosphere in the presence of a hydrogen donor such as cyclohexene, cyclohexadiene, or ammonium formate, using a solvent such as ethanol or methanol or the solvents above and a noble metal catalyst as described above.

A different nitrogen protecting group can be introduced, if desired, in step b to give 3 by acylation of 2 to form an amide, carbamate, urethane, or thiocarbamate using a variety of reagents such as acyl halides (e.g., acetyl chloride, propionyl bromide, benzoyl chloride or butyryl chloride), anhydrides (e.g., acetic anhydride, propionic anhydride or butyric anhydride), chloroformates (e.g., methyl chloroformate, ethyl chloroformate, vinyl chloroformate, benzyl chloroformate, 3,3,3-trichloroethyl chloroformate), or dicarbonates (e.g., di-t-butyl dicarbonate). Suitable general procedures for acylation of amines are described in March, J. in *Advanced Organic Chemistry*, Wiley, New York, 1985; Patai, S. (Ed.) in *The Chemistry of Amides*, Wiley, New York, 1970. These reactions can be carried out in nonpolar, aprotic solvents such as ethers (e.g., diethyl ether, tetrahydrofuran, dioxane, dimethoxyethane, dibutyl ether, t-butyl methyl ether), halogenated solvents (e.g., dichloromethane, chloroform, carbon tetrachloride, 1,2-dichloroethylene), hydrocarbon solvents (e.g., benzene, toluene, hexane), or aprotic dipolar solvents (e.g., dimethylformamide, dimethyl acetamide, dimethyl sulfoxide), and in the presence of a base (e.g., pyridine, 2,6-lutidine, triethylamine, potassium carbonate, aqueous sodium hydroxide, lithium carbonate, cesium carbonate, 4-dimethylaminopyridine, diisopropylethylamine, 1,8-diazabicyclo[5,4,0]undec-7-ene). N-Acylation is preferentially carried out by reacting compound 2 with a dicarbonate in pyridine as solvent at about −20° to 80° to give the product 3.

The opening of the epoxide ring in 3 (Reaction Scheme B) shown in step c to give gluco and altro products 4 and 5 can be achieved by reaction with an alkali metal thioalkoxide or arylthioxide, e.g. sodium thiomethoxide, lithium thiomethoxide, potassium thiomethoxide, calcium thiomethoxide, sodium thiophenoxide, in a hydroxylic solvent such as ethanol, methanol, isopropanol, or 2-methoxy-ethanol, or in a dipolar aprotic solvent such as dimethylformamide or dimethyl sulfoxide, at a temperature of from about 25° to 125° C. The alkali metal thiol salt can be preformed if desired or generated in situ. Such a reaction is well known in the literature as described in, e.g., *Chemical Communications*, 706 (1968).

Other suitable alkali metal thiol salts for use in the epoxide opening reaction to give sulfur substituted 1,5-iminosugars are the following compounds:

benzenemethanethiol, sodium salt
2,4-dichlorobenzenemethanethiol, sodium salt
3,4-dichlorobenzemethanethiol, sodium salt
p-methoxybenzenemethanethiol, sodium salt
o-methylbenzenemethanethiol, sodium salt
m-methylbenzenemethanethiol, sodium salt
p-methylbenzenemethanethiol, sodium salt
o-nitrobenzenemethanethiol, sodium salt
m-nitrobenzenemethanethiol, sodium salt
p-nitrobenzenemethanethiol, sodium salt
4-chlorobenzenemethanethiol, potassium salt
sodium p-chlorothiophenoxide
sodium 4-bromothiophenoxide
sodium p-t-butylthiophenoxide
sodium 4-fluorothiophenoxide
sodium p-hydroxythiophenoxide
sodium 4-methoxythiophenoxide sodium m-trifluoromethylthiophenoxide
cyclohexyl mercaptan, sodium salt
cyclopentyl mercaptan, sodium salt
allyl mercaptan, sodium salt
n-butyl mercaptan, sodium salt
sec-butyl mercaptan, sodium salt
t-butylmercaptan, sodium salt
2-chloroallylmercaptan, sodium salt
n-hexylmercaptan, sodium salt
isopropylmercaptan, sodium salt
1-mercapto-2-propanol, sodium salt
methallylmercaptan, sodium salt
n-propylmercaptan, sodium salt
2-naphthalenethiol, sodium salt
2-phenylethylmercaptan, sodium salt The opening of the epoxide ring in a nitrogen-unsubstituted compound such as 2 (Reaction Scheme C) to give gluco and altro products 25 and 26, respectively, can be carried out as described above for compound 3.

Simultaneous deprotection of the hydroxyl groups in compounds 4 and 5 along with the deprotection of the nitrogen protecting group V—C=O (Reaction Scheme A) where the group V—C=O is acid labile, such as t-butyloxycarbonyl or 3,4-dimethoxybenyloxycarbonyl can be accomplished by acid hydrolysis with an organic or mineral acid such as p-toluenesulfonic acid, hydrochloric acid, sulfuric acid, trifluoromethanesulfonic acid, in a solvent such as anhydrous ethanol or methanol or other solvents mentioned hereinbefore.

Selective deprotection of the hydroxyl groups in a compound such as 19 where $R_3$ is not an acid labile group to give 20 is accomplished in step n by acid hydrolysis where the acids and solvents are as described above for deprotection of compounds 4 and 5.

Deprotection of nitrogen in a compound such as 20 in which the protecting group is not acid labile can be accomplished by hydrolysis in water optionally containing a cosolvent such as ethanol, methanol, ethylene glycol, dioxane, or tetrahydrofuran, or in the absence of water and in a solvent or solvents as described above containing a base (e.g., sodium hydroxide, lithium hydroxide, lithium peroxide, potassium hydroxide), and the like. When the protecting group is, e.g., p-toluenesulfonyl, deprotection can be carried out by using sodium in liquid ammonia. Groups such as formyl and acetoacetyl can be removed by treatment with, e.g., hydroxylamine or phenylhydrazine. The chloroacetyl group can be removed with thiourea in a suitable solvent such as those mentioned hereinbefore.

Alkylation of nitrogen in compound 6 as shown in step e of Reaction Scheme A to give compound 7 can be accomplished by reductive amination of 6 using an aldehyde in the presence of a reducing agent such as sodium cyanoborohydride, sodium borohydride, borane pyridine complex, borane tetrahydrofuran complex, and the like, in a solvent such as ethanol, methanol, acetic acid, trifluoroacetic acid, or tetrahydrofuran, in the presence or absence of water. Additionally, alkylation can be achieved by reaction with an alkyl halide, such as an alkyl chloride, alkyl bromide, or alkyl iodide, in the presence or absence of a catalyst such as tetraalkylammonium iodide or a silver salt, and in the presence of a base, such as, e.g., potassium carbonate, pyridine, triethylamine, and the like, and in a solvent such as acetone, methyl ethyl ketone, acetonitrile, tetrahydrofuran, or alcohols such as ethanol or methanol, or in a dipolar aprotic solvent such dimethylformamide or dimethyl sulfoxide.

In addition alkylation on nitrogen can be accomplished by reduction of an amide compound such as 4 where V=alkyl, aryl, alkylaryl, cycloalkyl, alkylcycloalkyl, and the like, using a reducing agent such as lithium aluminum hydride, sodium cyanoborohydride, borane pyridine complex, borane tetrahydrofuran complex, borane dimethyl sulfoxide complex, and the like, in a solvent such as tetrahydrofuran, diethyl ether, dioxane, ethanol, methanol, or in a mixture of such solvents.

Acylation of the hydroxyl groups in compound 7 as shown in step f of Reaction Scheme A to give peracylated, or optionally partially acylated compounds such as 8, can be performed (see, e.g., Greene, T. W., and Wuts, P. G. M., *Protective Groups in Organic Synthesis*, 2nd Ed., Wiley, New York, 1991) by reaction of compound 7 with an acylating agent to form esters (such as acetate, chloroacetate, dichloroacetate, trichloroacetate, methoxyacetate, phenoxyacetate, 4-chloroacetate, isobutyrate, pivaloate, benzoate, propionate, butyrate, and the like), and carbonates (such as methyl, ethyl, 2,2,2-trichloroethyl, isobutyl, vinyl, allyl, phenyl, benzyl, and the like) using acid chlorides, anhydrides, and chloroformates. Acylation can also be performed using the carboxylic acid in the presence of a carbodiimide (e.g., dicyclohexylcarbodiimide, 3-(N,N-dimethylaminopropyl)ethylcarbodiimide), optionally in the presence of an activating agent such as N-hydroxybenzotriazole or N-hydroxysuccinimide. The acylation reactions can be carried out in non-polar, aprotic solvents such as ethers (e.g., diethyl ether, tetrahydrofuran, dioxane, dimethoxyethane, dibutyl ether, t-butyl methyl ether), halogenated solvents (e.g., dichloromethane, chloroform, carbon tetrachloride, 1,2-dichloroethylene), hydrocarbon solvents (e.g., benzene, toluene, hexane), or aprotic dipolar solvents (e.g., dimethylformamide, dimethyl acetamide, dimethyl sulfoxide), and in the presence of a base (e.g., pyridine, 2,6-lutidine, triethylamine, potassium carbonate, aqueous sodium hydroxide, lithium carbonate, cesium carbonate, 4-dimethylaminopyridine, diisopropylethylamine, 1,8-diazabicyclo[5,4,0]undec-7-ene).

Oxidation of the sulfur atom in 8 as shown in step g of Reaction Scheme A to give the mixture of epimeric sulfoxides9 is performed by treatment of the sulfide 8 with one equivalent of an oxidizing agent (e.g., m-chloroperoxybenzoic acid, peracetic acid, potassium peroxymonosulfate, hydrogen peroxide, and other methods as disclosed in, e.g., *Tetrahedron*, 1986, 42, 5459), in solvents such as acetone, acetic acid, methanol, ethanol, dichloromethane, ethyl acetate, dimethylformamide, 2-alkoxyethanol, and water.

Oxidation of compound 8 using an excess of oxidizing agent (more than three equivalents) using oxidants and solvents as described above (and described in *Tetrahedron*, 1986, 42, 5459) proceeds to give the sulfone N-oxide 11 as shown in step i.

The O-acyl groups in compound 9 are removed by hydrolysis in basic or acidic conditions to give the free triol 10 as illustrated in step h. Cleavage of the O-acyl groups is achieved by exposure of the compound to sodium, lithium, or potassium hydroxide in water or alcohol or a mixture of water and alcohol, or by exposure to a solution of sodium alkoxide in alcohol, or by exposure to a solution of an organic base such as triethylamine or quaternary ammonium hydroxide in water or alcohol or a mixture of water and alcohol, or by exposure to acid in a solvent as described above (e.g., hydrochloric or sulfuric acids).

Deoxygenation of the N-oxide in 11 to give 12 as shown in step j is accomplished by treatment of the N-oxide with a trisubstituted phosphine (e.g. triphenylphosphine or tri-p-tolylphosphine, tri-n-butylphosphine) in a solvent (e.g., acetic acid) at a temperature of from about 25° C. to 120° C. as described in, e.g., *Angewandte Chemie,* 68, 480 (1956).

Cleavage of the O-acyl groups in compound 12 to give 13 as described in step k is achieved as described above for compound 9.

The foregoing reaction conditions for carrying out the synthesis of Reaction Schemes B–D are further exemplified in specific Examples 5–27 as follows:

Example 5

The N-carbobenzoxy group in the product of Example 4 is removed such as by cleavage with, e.g., cyclohexene.

Example 6

The product of Example 5 is N-acylated with a dicarbonate such as, e.g., di-tertbutyl-dicarbonate.

Example 7

The epoxide in the product of Example 6 is opened by reaction with an alkali metal thiomethoxide to give a mixture of thio-substituted isomeric alcohols.

Example 8

The product of Example 4 is reacted with an alkali metal thiomethoxide to give a mixture of thio-substituted compounds (1, 2, 3 and 4).

Example 9

The hydroxyl protecting group at C4 and C6 of product compound 1 of Example 8 is removed by acid cleavage of acetal or ketal.

Example 10

The N-carbamate group in the product of Example 9 is removed by basic cleavage.

Example 11

The product of Example 10 is N-alkylated such as with, e.g., butyraldehyde.

Example 12

The hydroxy protecting group at C-4 and C-6 and the N-BOC group of product compound 2 of Example 7 are removed by acid cleavage.

Example 13

The altritol product of Example 12 is N-alkylated such as with, e.g., butyraldehyde.

Example 14

The product of Example 5 is reacted with a thiomethoxide to give a mixture of 2- and 3-thio-substituted compounds.

Example 15

The product of Example 4 is reacted with thiophenol to give a mixture of 4 thio-substituted compounds (1, 2, 3 and 4).

Example 16

The hydroxyl protecting group at C4 and C6 of product compound 1 of Example 15 is removed by acid cleavage of acetal or ketal.

Example 17

The N-carbamate group in the product of Example 16 is removed by basic cleavage.

Example 18

The product of Example 17 is N-alkylated such as with, e.g., butraldehyde.

Example 19

The epoxide in the product of Example 6 is opened by reaction with alkali metal thiophenoxide to give a mixture of thio-substituted isomeric alcohols 1 and 2.

Example 20

The N-butyloxycarbinol group in product compound 1 of Example 19 is removed by acid cleavage.

Example 21

The product of Example 11 is O-acylated at the free hydroxyl groups such as with, e.g., acetic anhydride.

Example 22

The 2-thio-substituted product of Example 21 is converted to the corresponding 2-sulfinyl-substituted compound by reaction with about one equivalent of m-chloroperoxybenzoic acid.

Example 23

The O-acyl groups in the product of Example 22 are removed by cleavage with triethylamine.

Example 24

The 2-thio-substituted product of Example 21 is converted to a 2-sulfonyl-substituted compound by reaction with about four equivalents of m-chloroperoxybenzoic acid.

Example 25

The N-butylimino, N-oxide group in the product of Example 24 is converted to the N-butylimino group by reaction with triphenylphosphine.

Example 26

The O-acylated groups in the product of Example 25 are removed by cleavage with triethylamine.

Example 27

The hydroxyl protecting group at C4 and C6 of product compound4 of Example 15 is removed by cleavage of acetal or ketal.

In standard biological tests, the novel compounds of this invention have been shown to have inhibitory activity against the human immunodeficiency virus (HIV) and/or against visna virus and/or against glucosidase enzymes.

Inhibitory activity against HIV-1 was shown by tests involving plating of susceptible human host cells which are syncytium-sensitive with and without virus in microculture plates, adding various concentrations of the test compound, incubating the plates for 9 days (during which time infected, non-drug treated control cells are largely or totally destroyed by the virus), and then determining the remaining number of viable cells with a colorometric endpoint.

Inhibitory activity against visna virus was shown by a conventional plaque reduction assay. Visna virus, a lentivirus genetically very similar to the AIDS virus, is pathogenic for sheep and goats. See Sonigo et al., *Cell* 42, 369–382 (1985); Haase, *Nature* 322, 130–136 (1986). Inhibition of visna virus replication in vitro as a useful model for HIV and its inhibition by test compounds has been described by Frank et al., *Antimicrobial Agents and Chemotherapy* 31(9), 1369–1374 (1987).

Inhibitory activity against α and β-glucosidase enzymes was determined by conventional in vitro assays for these enzymes as described in U.S. Pat. No. 4,973,602. These assays involve spectrophotometric measurement of the release of p-nitrophenol from the substrate p-nitrophenylglycoside in the presence and absence of the test compound and comparison against a control standard that contains a known inhibitor of the enzyme.

DETAILED DESCRIPTION OF THE INVENTION

The following detailed examples will further illustrate the invention although it will be understood that the invention is not limited to these specific examples or the details described therein.

Example 1

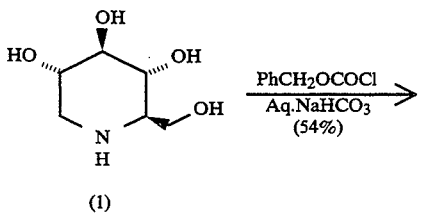

(1)

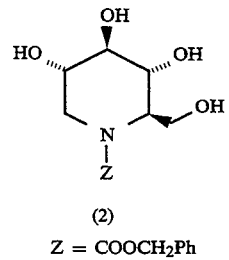

(2)

Z = COOCH₂Ph

Preparation of 1,5-dideoxy-1,5-[{(phenylmethoxy)carbonyl}imino]-D-glucitol (2)

To a stirred solution of 1-deoxynojirimycin (1) (100 g, 0.61 mol) in saturated aqueous sodium bicarbonate (1000 ml), benzyl chloroformate (95%, 121 g, 0.67 mol) was added dropwise at room temperature. After stirring at room temperature for 18 hr, the solution was extracted once with methylene chloride (300 ml) to remove any unreacted benzyl chloroformate. The aqueous layer was then extracted several times with ethyl acetate to give a total of 2.5–3 liters of the extract. The organic layer was then dried (Na₂SO₄), filtered and concentrated to give (2) a white solid (98.57 g, 54%), mp 101°–2° C., Anal calcd. for C₁₄H₁₉NO₆ C, 56.56, H, 6.44, N, 4.71 Found C, 56.33, H, 6.38, N, 4.58., ¹H NMR (CD₃OD) 7.2–7.4 (m, 5H), 5.15 (s, 2H), 4.23 (br m, 1H), 4.05 (br d., J=8 Hz, 1H), 3.87 (dd, J=6, 4 Hz, 1H), 3.78–3.85 (m, 2H), 3.70–3.78 (m, 2H), 3.45 (br d, J=8 Hz, 1H).

Example 2

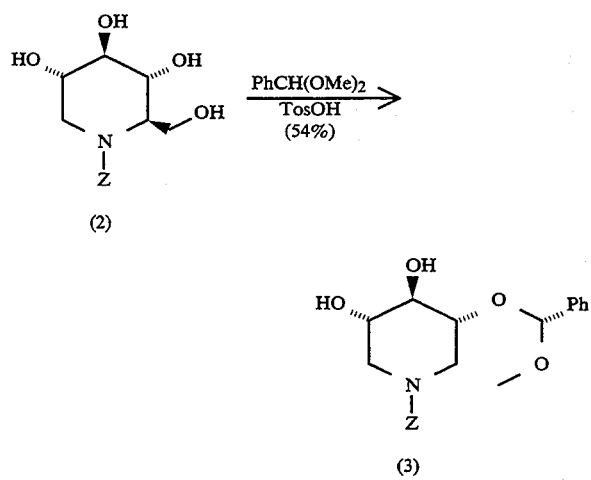

Preparation of 1,5-dideoxy-1,5-[{(phenylmethoxy)carbonyl}imino]-4,6-O-(R-phenylmethylene)-D-glucitol (3)

A mixture of (2) (98.5 g, 0.33 mol), benzaldehyde dimethyl acetal (65.5 g, 0.43 mol) and p-toluenesulfonic acid (1 g) in a round bottom flask was dissolved in dimethlformamide (400 ml). The flask was connected to a water aspirator and the reaction was heated to 60°–65° C. for 4 hr. The reaction mixture was cooled to room temperature and poured into stirred ice-water (1200 ml) containing sodium bicarbonate (14 g). The white solid formed was filtered, washed with cold water and dried. Recrystallization using hexane/ethyl acetate gave 3 (96.2 g, 54%) as pure white solid, mp 147°–48° C., Anal calcd. for C₂₁H₂₃NO₆ C, 65.44, H, 6.02, N, 3.63 Found C, 65.15, H, 5.93, N, 3.49. IR (KBr) 3420, 1715, 1450, 1425, 1395, 1380, 1365, 1090cm⁻¹; ¹H NMR (CD₃OD) 7.28–7.53 (m, 10H), 5.61 (s, 1H), 5.14 (s, 2H), 4.77 (dd, J=11, 4.6 Hz, 1H), 4.38 (t, J=11 Hz, 1H), 4.16 (dd, J=13.4, 4.2 Hz, 1H), 3.5–3.7 (complex m, 3H), 3.35 (td, J=11, 4.6 Hz), 2.97 (dd, J=13.4, 9.3 Hz, 1H); ¹³C NMR (CD₃OD) 156.7, 139.4, 138.0, 129.9, 129.7, 129.3, 129.2, 129.1, 127.6, 102.8, 81.9, 77.5, 71.5, 70.6, 68.6, 55.9 and 50.5; MS (CI, NH₃, m/e) 386 (M+1).

Example 3

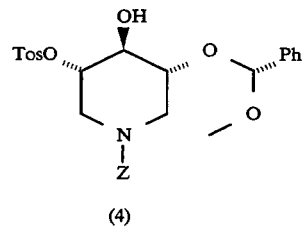

(4)

Preparation of 1,5-dideoxy-1,5-[{(phenylmethoxy)carbonyl}imino]-4,6-O-(R-phenylmethylene)-D-glucitol, 2-(4-methylbenzenesulfonate) (4)

A mixture of diol 3 (46.3 g, 0.12 mol) and di-n-butyltin oxide (31.1 g, 0.125 mol) in methanol (300 ml) was

Example 5

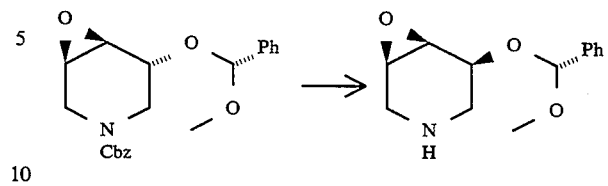

Preparation of 2,3-Anhydro-1,5-dideoxy-1,5-imino-4,6-R-phenyl-methylene-D-mannitol To a solution of 500 mg (1.36 mmoles) of the title Cbz-protected amine compound of Example 4 in 20 ml of 9:1 absolute ethanol - cyclohexene was added 100 mg of 10% Pd/C. The mixture was stirred at reflux under $N_2$ for 2 hours. After cooling, the mixture was filtered and solvent evaporated to give 324 mg of the title compound (100%). The structure was supported by NMR.

Example 6

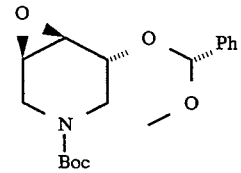

Preparation of 2,3-Anhydro-1,5-dideoxy-1,5-[(2-methyl-2-propyloxycarbonyl)imino]-4,6-R-phenylmethylene-D-mannitol A solution of 324 mg (1.36 mmoles) of the title product of Example 5 and 326 mg (1.50 mmoles, 1.1 eqs.) of di-t-butyl dicarbonate in 10ml of pyridine was stirred at room temperature for 2.0 hours. After evaporation of solvent, the residue was partitioned between ethyl acetate / 10% aqueous copper sulfate solution, the organic phase was washed with 10% aqueous copper sulfate solution, with water, and with brine, dried over sodium sulfate, and concentrated. Chromatography of the residue over silica gel using 25% ethyl acetate/hexanes as eluent gave the title compound, 144 mg (31%). The structure was supported by NMR.

Example 7

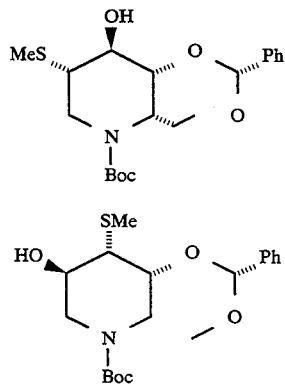

refluxed for 2 hr. The methanol was removed, toluene was added and removed under vacuum. The residue was dissolved in methylene chloride (300 ml) and triethylamine (20 ml, 0.144 mmol). After cooling to 0° C., p-toluenesulfonyl chloride (25.2 g, 0.132 mmol) was added. The reaction was stirred at 0° C. for 30 min and then warmed to 20° C. After stirring for 3 hr, the reaction was quenched by adding saturated aqueous sodium bicarbonate. The organic layer was separated and washed with water, 0.5M $KHSO_4$ and water successively. The organic layer was dried ($Na_2SO_4$), filtered and concentrated. The residue was chromatographed (silica gel, hexane/ethyl acetate 7/3) to give pure 4 (50.27 g, 77%) as white solid, mp 115°-17° C., Anal calcd. for $C_{28}H_{29}NO_8S$: C, 62.32, H, 5.42, N, 2.66 Found C, 62.65, H, 5.40, N, 2.62. $^1H$ NMR ($CDCl_3$) 7.82 (d, J=7.8 Hz, H), 7.35-7.50 (m, 10H), 7.31 (d, J=7.8 Hz, 2H), 5.51 (s, 1H), 5.12 (s, 2H), 4.76 (dd, J=11.4, 4.5 Hz, 1H), 4.38 (ddd, J=9.3, 7.6, 4.8 Hz, 1H), 4.32 (dd, J=11.4, 9.5 Hz, 1H), 4.31 (dd, J=13.6, 4.8 Hz, 1H), 3.78 (dt, J=2.6, 9.4Hz, 1H), 3.59 (t, J=9.4 Hz, 1H), 3.26 (ddd, J=11.4, 9.4, 4.5 Hz, 1H), 3.04 (dd, J=13.6, 9.3 Hz, 1H) 2.63 (d, J=2.6 Hz, 1H), 2.41 (s, 3H); $^{13}C$ NMR ($CDCl_3$) 154.8, 145.2, 137.0, 135.8, 133.2, 129.8, 129.3, 128.7, 128.4, 128.3, 128.1, 126.2, 101.8, 79.9, 78.1, 73.9, 69.2, 67.8, 54.2, 47.1 and 21.7; MS (m/e) 546 (M+Li).

Example 4

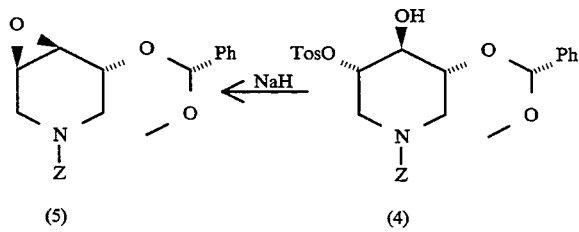

Preparation of 2,3-anhydro-1,5-dideoxy-1,5-[{(phenylmethoxy)carbonyl}imino]-4,6-O-(R-phenylmethylene)-D-mannitol (5)

Sodium hydride (2.79 g, 60% dispersion in mineral oil, 69.66 mol) was placed in a flask under argon and washed three times with dry hexane. The residue was suspended in dry THF (300 ml) and to this a solution of 4 (37.6 g, 69.66 mmol) in THF (100 ml) was added slowly. After stirring for 18 hr, the reaction was quenched by adding water. The organic layer was extracted with ethyl acetate and washed with saturated aqueous sodium bicarbonate and brine. After drying (sodium sulfate) and filtration, the organic layer was concentrated and recrystallized using cyclohexane to give pure 5 (19.2 g, 75%) as white solid, mp 104°-5° C., Anal calcd for $C_{21}H_{21}NO_5$ C, 68.64, H, 5.77, N, 3.81 Found C, 68.21, H, 5.84 N, 3.67. $^1H$ NMR ($CDCl_3$) 7.53-7.67 (m, 10H), 5.67 (s, 1H), 5.16 (s, 2H), 4.76 (broad s, 1H), 4.59 (d, J=15 Hz, 1H), 4.08 (d, J=10 Hz, 1H), 4.02 (dd, J=11.4, 4 Hz, 1H), 3.46 (dd, J=15, 0.9 Hz, 1H), 3.40 (d, J=3 Hz, 1H), 3.25 (d, J=3 Hz, 1H), 3.10 (dt, J=4, 10 Hz, 1H); $^{13}C$ NMR ($CDCl_3$) 156.2, 137.8, 136.6, 129.7, 129.1, 128.9, 128.8, 128.5, 126.6, 102.8, 73.0, 70.4, 68.0, 56.0, 54.7, 50.4 and 46.6; MS (CI, $NH_3$, m/e) 368 (M+H).

Preparation of 1,5-Dideoxy-1,5-[(2-methyl-2-propyloxycarbonyl-)imino]-2-S-methyl-4,6-O-(R-phenylmethylene)-2-thio-D-glucitol 1 and 1,5-Dideoxy-1,5-[(2-methyl-2-propyloxycarbonyl-)imino]-3-S-methyl-4,6-O-(R-phenylmethylene)-3-thio-D-altritol 2

A solution of 142 mg (0.426 mmole) of the title product of Example 6 and 149 mg (2.13 mmoles, 5.0 eqs) of sodium thiomethoxide in 5 ml of 2-methoxyethanol was stirred at reflux for 0.5 hour. After cooling, the mixture was partitioned between ethyl acetate/water, the aqueous layer was extracted twice with ethyl acetate, the combined organic extracts were washed with water and with brine, dried over sodium sulfate, and concentrated. Radial chromatography of the residue over silica gel (2 mm layer thickness, elution with 25% ethyl acetate/hexanes) gave 76 mg of the glucitol product 1 (47%) and 43 mg of the altritol product 2 (26%) (total yield=73%). The structures were supported by NMR.

Example 8

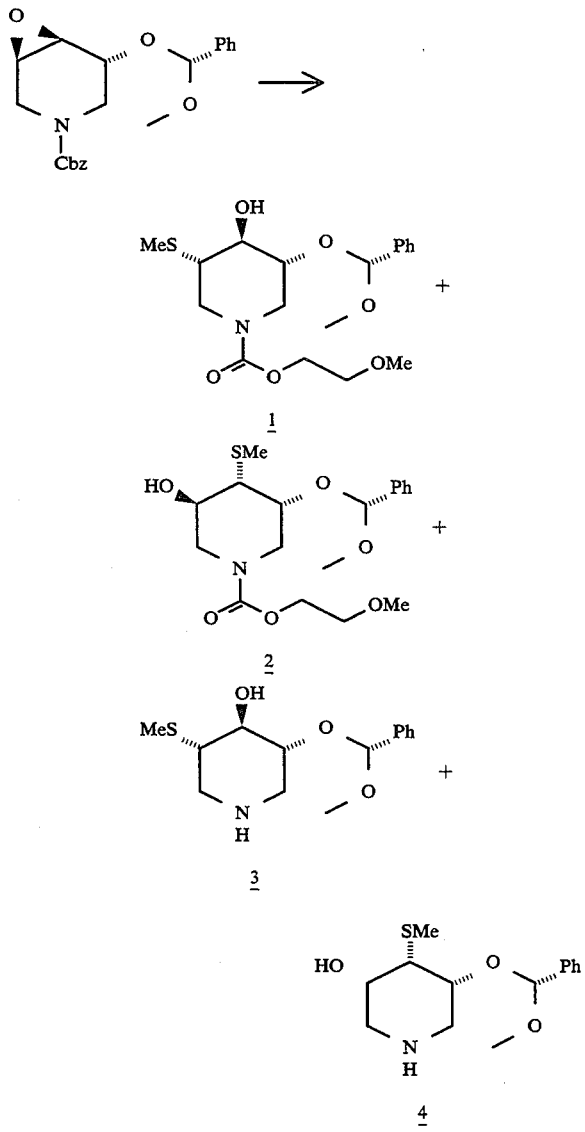

Preparation of 1,5-Dideoxy-1,5-[[(2-methoxyethoxy)carbonyl]imino]-2-S-methyl-4,6-O-(R-phenylmethylene)-2-thio-D-glucitol 1

Preparation of 1,5-Dideoxy-1,5-[[(2-methoxyethoxy)carbonyl]imino]-3-S-methyl-4,6-O-(R-phenylmethylene)-3-thio-D-altritol 2

Preparation of 1,5-Dideoxy-1,5-imino-2-S-methyl-4,6-O-(R-phenylmethylene)-2-thio-D-glucitol 3

Preparation of 1,5-Dideoxy-1,5-imino-3-S-methyl-4,6-O-(R-phenylmethylene)-3-thio-D-altritol 4

A solution of 1.53 g (4.15 mmoles) of the title compound of Example 4 and 1.46 g (20.8 mmoles) of sodium thiomethoxide in 20 ml of 2-methoxyethanol was refluxed for 1.0 hour. After cooling, the mixture was partitioned between ethyl acetate/water, the aqueous further extracted with two portions of ethyl acetate, the combined extracts washed with brine and dried over sodium sulfate. After concentration, chromatography of the residue over silica gel using a gradient of 50–70% ethyl acetate/hexanes gave 410 mg (26%) title compound 1 and 29 mg (1.8%) title compound 2, then eluting with 10% methanol/ethyl acetate gave 286 mg (24%) title compound 3 and 35 mg (3%) title compound 4. The structures were supported by NMR.

For 3: Anal. for $CH_{14}H_{19}NO_3S$ (MW 281.38): Calc'd.: C, 59.77;, H, 6.81; N, 4.98. Found: C, 59.65; H, 6.85; N, 5.00.

For 4: Anal. for $C_{14}H_{19}NO_3S \cdot \frac{1}{8} H_2O$ (MW 283.63): Calc'd.: C, 59.31; H, 6.84; N, 4.94. Found: C, 59.15; H, 6.86; N, 4.92.

Example 9

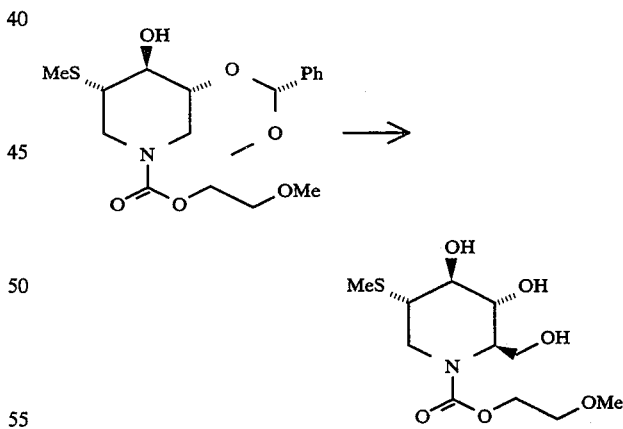

Preparation of 1,5-Dideoxy-1,5-[[(2-methoxyethoxy)carbonyl]imino]-2-S-methyl-2-thio-D-glucitol A solution of 400 mg (1.04 mmole) of the title compound 1 of Example 8 and 40 mg (0.21 mmole, 20 mole %) of p-toluenesulfonic acid monohydrate in 18 ml of ethanol was refluxed overnight. After cooling and addition of 0.25 ml of triethylamine the mixture was directly eluted from silica gel using 5% methanol/ethyl acetate as eluent to give the title compound, 260 mg (85%). The structure was supported by NMR.

Example 10

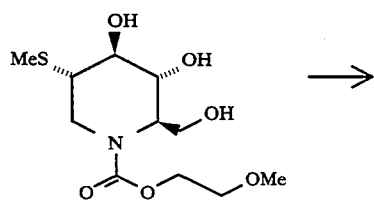

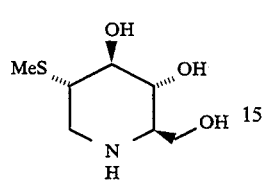

Preparation of 1,5-Dideoxy-1,5-imino-2-S-methyl-2-thio-D-glucitol

A solution of 260 mg (0.881 mmoles) of the title compound of Example 9 and 400 mg of potassium hydroxide in 10 ml of methanol was refluxed overnight. Direct chromatography of the mixture over silica gel using 25% methanol/2.5% ammonium hydroxide/72.5% ethyl acetate as eluent gave the title compound, 96 mg (56%). Anal. for $C_7H_{15}NO_3S \cdot \frac{3}{4} H_2O$ (MW 206.78): Calc'd.: C, 40.66; H, 8.04; N, 6.80. Found: C, 40.46; H, 7.65; N, 6.99. 13C NMR (D2O) d 74.82, 71.95, 60.47, 60.34, 47.75, 47.23, 11.98. 1H NMR (400 MHz) (D2O) d 4.84 (HOD), 3.86 (dd, J=11, J=4, 1H), 3.75 (dd, J=12, J=4, 1H), 3.41 (m, 3H), 2.78 (m, 2H), 2.66 (m, 1H), 2.16 (s, 3H).

Example 11

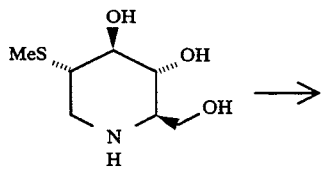 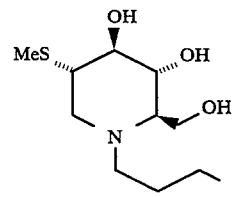

Preparation of 1,5-(Butylimino)-1,5-dideoxy-2-S-methyl-2-thio-D-glucitol

To a mixture of 93 mg (0.482 mmole) of the title compound of Example 10, 85 ml of butyraldehyde, and 250 mg of activated 4 Å molecular sieves in 1.6 ml of methanol and 79 ml of acetic acid was added 32 mg of sodium cyanoborohydride. After stirring overnight at room temperature, the mixture was filtered through Celite and concentrated. The residue was chromatographed over silica gel using 50/50 methanol/ethyl acetate as eluent. Appropriate fractions were concentrated, dissolved in 50/50 trifluoroacetic acid/water, then evaporated. The residue in 50/50 methanol/water was passed through a basic ion exchange column eluting with 50/50 methanol/water, and then through an acidic ion exchange column, first washing with water then eluting with 50/50 methanol/water, 0.5M in ammonium hydroxide. After concentration, the residue was triturated with ethyl acetate to give the title compound, 76 mg (63%) as a white crystalline solid. Anal. for $C_{11}H_{23}NO_3S \cdot \frac{1}{4} H_2O$ (MW 249.38): Calc'd.: C, 52.97; H, 9.29; N, 5.62. Found: C, 52.69; H, 9.30; N, 5.57.

Example 12

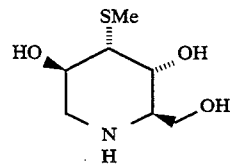

Preparation of 1,5-Dideoxy-1,5-imino-3-S-methyl-3-thio-D-altritol

A solution of the second title compound 2 of Example 7 (840 mg, 2.99 mmoles) and 682 mg (3.59 mmoles) of p-toluenesulfonic acid monohydrate in 60 ml of 95% ethanol was refluxed overnight. Another 136 mg (0.716 mmole) of p-toluenesulfonic acid monohydrate was added and refluxing continued for 6 hours. After cooling, basic ion exchange resin was added, the mixture was stirred for a few minutes, filtered, and concentrated. Crystallization of the residue from methanol gave the title compound, 365 mg, as a white crystalline solid, M.P. 182° C.

Anal.: Calc'd. for $C_7H_{15}NO_3S$ (MW 193.27): C, 43.50; H, 7.82; N, 7.25. Found: C, 43.41; H, 8.01; N, 7.26.

Example 13

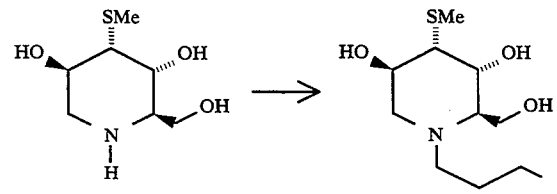

Preparation of 1,5-(Butylimino)-1,5-dideoxy-3-S-methyl-3-thio-D-altritol

To a solution of 141 mg (0.731 mmoles) of the title amine compound of Example 12, 109 ml (105 mg, 1.46 mmoles, 2.0 eqs) butyraldehyde, and 500 mg of 4 Å sieves in 2.5 ml of methanol and 120 µl of acetic acid was added 48 mg (0.76 mmole, 1.04 eqs) of sodium cyanoborohydride. After stirring overnight at room temperature, the mixture was filtered through Celite and concentrated. Chromatography of the residue over silica gel using 10% methanol/2.5% ammonium hydroxide/87.5% ethyl acetate as eluent gave the title compound, 101 mg (64%). Anal. for $C_{11}H_{23}NO_3S \cdot \frac{1}{4} H_2O$ (MW 253.88): Calc'd.: C, 52.03; H, 9.33; N, 5.520 Found: C, 51.90; H, 9.30; N, 5.42.

Example 14

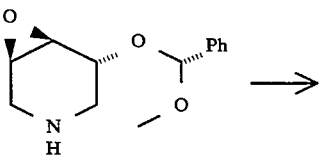

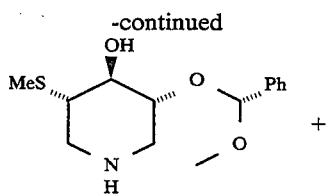

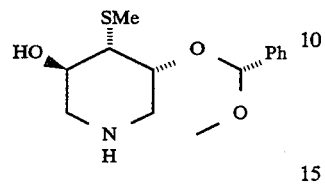

Preparation of
1,5-Dideoxy-1,5-imino-2-S-methyl-4,6-O-(R-phenylmethylene)-2-thio-D-glucitol 1 and Preparation of
1,5-Dideoxy-1,5-imino-3-S-methyl-4,6-O-(R-phenylmethylene)-3-thio-D-altritol 2

A solution of 486 mg (2.09 mmoles) of the title compound of Example 5 and 732 mg (10.5 mmoles, 5.0 eqs) of sodium thiomethoxide in 21 ml of 2-methoxyethanol was stirred at reflux for 1.0 hour. After cooling, the mixture was partitioned between ethyl acetate/water, the aqueous extracted twice with ethyl acetate, the combined extracts washed with brine, and dried over sodium sulfate. Chromatography of the residue over silica gel using a gradient of 0–10% methanol/ethyl acetate as eluent gave 50 mg (8.5%) of title compound 1, and 210 mg (36%) of title compound 2. The structures were confirmed by NMR.

Example 15

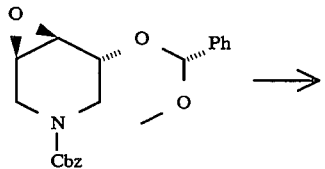

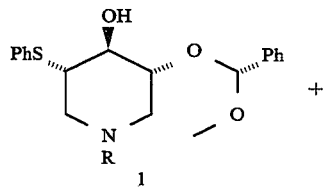

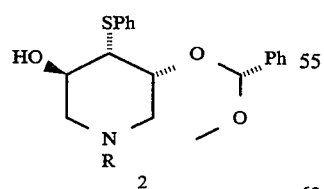

R=COOCH₂CH₂OMe

Preparation of
1,5-Dideoxy-1,5-[[(2-methoxyethoxy)carbonyl]imino]-2-S-phenyl-4,6-O-(R-phenylmethylene)-2-thio-D-glucitol 1

Preparation of
1,5-Dideoxy-1,5-[[(2-methoxyethoxy)carbonyl]imino]-3-S-phenyl-4,6-O-(R-phenylmethylene)-3-thio-D-altritol 2

Preparation of
1,5-Dideoxy-1,5-imino]-2-S-phenyl-4,6-O-(R-phenylmethylene)-2-thio-D-glucitol 3

Preparation of
1,5-Dideoxy-1,5-imino-3-S-phenyl-4,6-O-(R-phenylmethylene)-3-thio-D-altritol 4

Sodium thiophenoxide was generated in situ by adding 5.1 ml (49.7 mmoles) of thiophenol to a solution of 1.20 g (52.2 mmoles) of Na in 50 ml of 2-methoxyethanol, bringing the solution to brief reflux, and cooling. To this solution was added 3.05 g (8.31 mmoles) of the title epoxide compound (5) of Example 4, and the resulting mixture was refluxed for 1.0 hour. After cooling, the mixture was partitioned between ethyl acetate/water, the aqueous was extracted twice with ethyl acetate, the combined extracts were washed with brine, dried over sodium sulfate and concentrated. Chromatography over silica gel using 50/50 ethyl acetate/hexanes as eluent gave title compound 1 as a white solid, 1.04 g (28%), using 75% ethyl acetate as eluent gave title compound 2 as a white foam, 315 mg (8.5%), using ethyl acetate as eluent gave title compound 3 as a white solid, 443 mg (16%), and using 25% MeOH/Ethyl acetate as eluent gave title compound 4, 647 mg (23%) as a white solid.

1—Anal. for C₂₃H₂₇NO₆S (MW 445.54): Calc'd.: C, 62.02; H, 6.11; N, 3.14. Found: C, 61.97; H, 6.27; N, 3.14.

3—Anal. for C₁₉H₂₁NO₃S (MW 343.45): Calc'd.: C, 66.43; H, 6.16; N, 4.08. Found: C, 66.22; H, 6.16; N, 4.14. The structures of title compounds 2 and 4 were supported by NMR.

Example 16

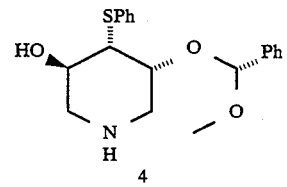

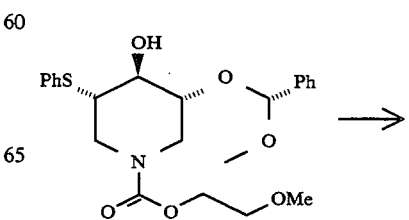

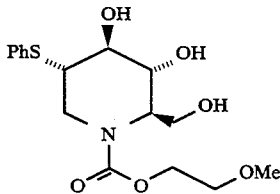

Preparation of 1,5-Dideoxy-1,5-[[(2-methoxyethoxy)carbonyl]imino]-2-S-phenyl-2-thio-D-glucitol A solution of 1.04 g (2.33 mmoles) title compound 1 of Example 15 and 89 mg (20 mole%) of p-toluenesulfonic acid monohydrate in 38 ml of ethanol was refluxed for 3 hours. After cooling, the solution was concentrated and the residue chromatographed over silica gel using 5% methanol/ethyl acetate as eluent to give 755 mg (95%) of the title compound.

Anal. for $C_{16}H_{23}NO_6S$ (MW 357.43): Calc'd.: C, 53.78; H, 6.49; N, 3.92. Found: C, 54.08; H, 6.60; N, 3.95.

Example 17

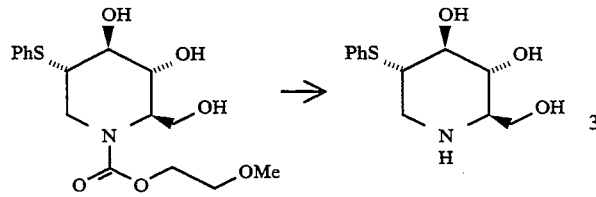

Preparation of 1,5-Dideoxy-1,5-imino-2-S-phenyl-2-thio-D-glucitol

A solution of 227 mg (0.636 mmole) of the title compound of Example 16 and 282 mg of potassium hydroxide in 6 ml of methanol was refluxed for 4.0 hours. After cooling, 1 ml of acetic acid was added and the solvent removed. Chromatography of the residue over silica gel using 25% methanol/2.5% ammonium hydroxide/72.5% ethyl acetate as eluent gave the title compound, 45 mg (26%) as a pale yellow solid. Anal. for $C_{12}H_{17}NO_3S \cdot H_2O$ (MW 273.36): Calc'd.: C, 52.78; H, 7.00; N, 5.12. Found: C, 52.50; H, 6.61; N, 5.38.

Example 18

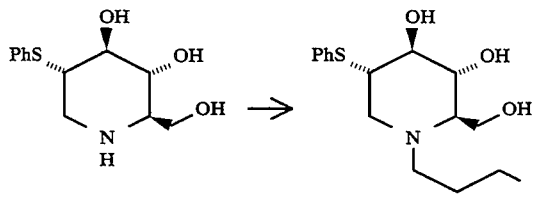

Preparation of 1,5-(Butylimino)-1,5-dideoxy-2-S-phenyl-2-thio-D-glucitol

To a mixture of 170 mg (0.667 mmoles) of the title compound of Example 17, 96 mg (1.3 mmoles, 2.0 eqs) of butyraldehyde, 300 mg of 4 Å molecular sieves, 2.2 ml of methanol, and 110 μl of acetic acid was added 44 mg (0.69 mmoles, 1.04 eqs) of sodium cyanoborohydride, and the resulting mixture was stirred overnight at room temperature. The mixture was filtered through Celite, concentrated, then chromatographed over silica gel eluting with 25% methanol/2.5% ammonium hydroxide/72.5% ethyl acetate. Appropriate fractions were concentrated and the residue taken up in 50/50 trifluoroacetic acid/water, then evaporated. Ion exchange chromatography over a basic resin eluting with 25% methanol/water followed by a basic resin eluting with 25% methanol/0.5M aqueous ammonium hydroxide and then lyophilization gave the title compound, 48 mg (23%) as a white, crystalline solid. Anal. for $C_{16}H_{25}NO_3S \cdot \frac{1}{4} H_2O$ (MW 315.95): C, 60.83; H, 8.14; N, 4.43. Found: C, 60.44; H, 7.92; N, 4.55.

Example 19

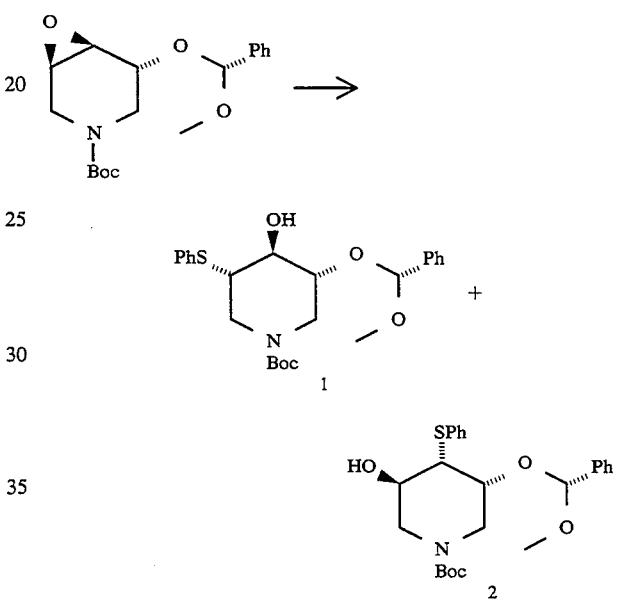

To a solution of sodium thiophoxide (prepared by adding 1.10 g, 10.0 mmoles of thiophenol to a solution of 230 mg, 10.0 mmoles of sodium in 20 ml of 2-methoxyethanol followed by stirring at room temperature for 15 min) was added 666 mg (2.00 mmoles) of the title epoxide compound of Example 6 as a solid., and the mixture was stirred at reflux for 1.0 hour. After cooling, the mixture was partitioned between ethyl acetate/water, the aqueous was extracted twice with ethyl acetate, the combined extracts were washed with brine and dried over sodium sulfate. The solution was concentrated and the residue chromatographed over silica gel using a gradient of 25–50% ethyl acetate/hexanes as eluent to give 490 (55%) of 1 and 360 mg (41%) of 2 (total yield=96%). The structures were supported by NMR.

Example 20

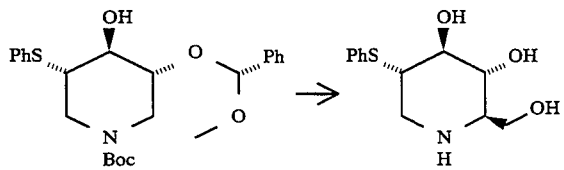

Preparation of 1,5-Dideoxy-1,5-imino-2-S-phenyl-2-thio-D-glucitol

A solution of 430 mg (0.968 mmole) of one of the title compounds, 1, of Example 19 and 221 mg (1.16 mmole, 1.2 mole %) p-toluenesulfonic acid monohydrate in 20 ml of ethanol was refluxed for 3.0 hour. After cooling, 1 ml of triethylamine was added and the mixture concentrated. The residue was taken up in 40% methanol/water and passed through a basic ion exchange column. The solvent was evaporated to give the title compound, 252 mg (102%) as a white solid. The structure was supported by NMR and by comparison with the title product of Example 17.

Example 21

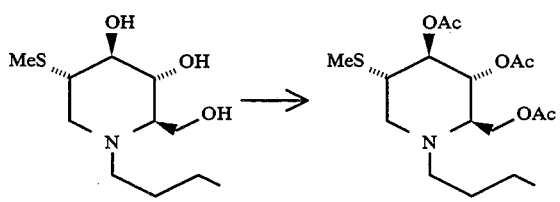

Preparation of 1,5-(Butylimino)-1,5-dideoxy-2-S-methyl-2-thio-D-glucitol, triacetate A solution of 1.80 g (7.23 mmoles) of the title compound of Example 11 in 50 ml of pyridine and 20 ml of acetic anhydride was refluxed for 15 min. After cooling, the mixture was concentrated. The residue was taken up in ethyl acetate, washed with aqueous copper sulfate solution, with water, with brine, and dried over sodium sulfate. The solution was concentrated and chromatographed over silica gel using 30% ethyl acetate/hexanes as eluent to give the title compound, 1.72 g (63%). Anal. for $C_{17}H_{29}NO_6S$ (MW 375.49): Calc'd.: C, 54.38; H, 7.78; N, 3.73. Found: C, 54.22; H, 7.76; N, 3.83.

Example 22

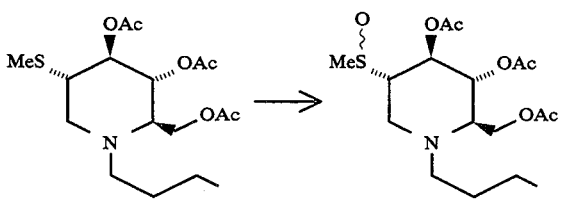

Preparation of 1,5-(Butylimino)-1,5-dideoxy-2S-methyl-2-sulfinyl-D-glucitol, triacetate To an ice cold stirred solution of the title compound of Example 21 in 24 ml of dichloromethane was added 285 mg (1.32 mmoles, 1.1 eqs) of 85% m-chloroperoxybenzoic acid as a solid. The mixture was stirred overnight while warming to room temperature and then directly chromatographed over silica gel eluting the sulfoxide with 10% methanol/2.5% ammonium hydroxide/87.5% ethyl acetate followed by a second chromatography over silica gel using 5% 2-propanol/2.5% ammonium hydroxide/92.5% chloroform as eluent to give the title compound, 123 mg (26%) as an oil. Anal. for $C_{17}H_{29}NO_7S$ (MW 391.49): Calc'd.: C, 52.16; H, 7.47; N, 3.58. Found: C, 52.18; H, 7.52; N, 3.14.

Example 23

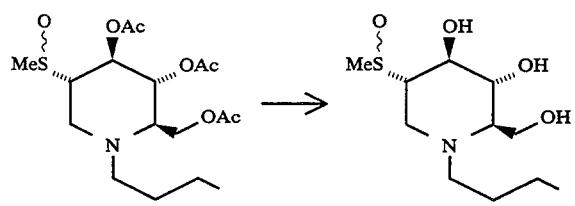

Preparation of 1,5-(Butylimino)-1,5-dideoxy-2-S-methyl-2-sulfinyl-D-glucitol

A solution of 67 mg (0.171 mmole) of the title compound of Example 22 in a mixture of 8 ml of methanol, 1 ml of water, and 1 ml of triethylamine was stirred overnight at room temperature. The solution was evaporated to give the title compound, 43 mg (96%). Anal. for $C_{11}H_{23}NO_4S$ (MW 265.38): Calc'd.: C, 49.77; H, 8.73; N, 5.28. Found: C, 49.58; H, 8.71; N, 5.16.

Example 24

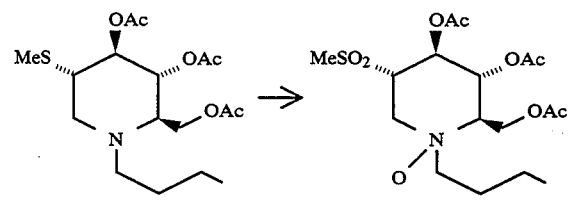

Preparation of 1,5-[Butyl(hydroxyimino)]-1,5-dideoxy-2-S-methyl-2-sulfonyl-D-glucitol, triacetate To an ice cold solution of 450 mg (1.20 mmoles) of the title compound of Example 21 in 24 ml of dichloromethane was added 830 mg (4.80 mmoles, 4.0 eqs) of 85% m-chloroperoxybenzoic acid in one portion as a solid. The mixture was stirred overnight while permitting to warm to room temperature. Direct chromatography over silica gel using 10% 2-propanol/2% ammonium hydroxide/87.5% chloroform as eluent gave the title compound (180 mg) as a pale tan solid. The product was reacted directly further as is. The structure was supported by NMR.

Example 25

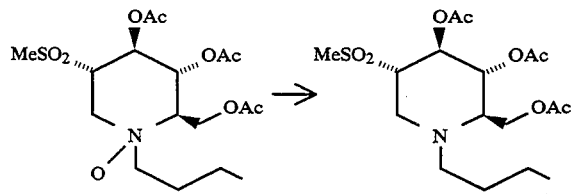

Preparation of 1,5-(Butylimino)-1,5-dideoxy-2-S-methyl-2-sulfonyl-D-glucitol, triacetate A mixture of 263 mg (0.631 mmole) of the title compound of Example 24 and 182 mg (0.694 mmole, 1.1 eqs)

of triphenylphosphine in 7 ml of acetic acid was stirred at reflux for 1.0 h then cooled. After removal of solvent by azeotropic distillation with toluene, the residue was chromatographed over silica gel using 55% ethyl acetate/hexanes to give the title compound, 177 mg (70%). The structure was supported by NMR.

Example 26

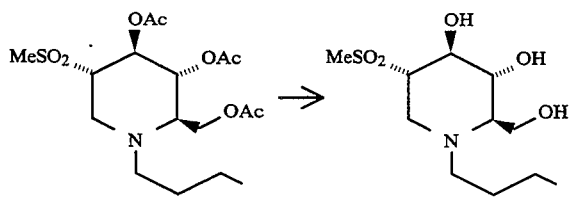

Preparation of 1,5-(Butylimino)-1,5-dideoxy-2-S-methyl-2-sulfonyl-D-glucitol

A solution of 137 mg (0.337 mmole) of the title compound of Example 25 in 10 ml of 8:1:1 methanol/water/triethylamine was kept overnight at room temperature. After evaporation of the solvent, the residue was chromatographed over silica gel using 10% methanol/2.5% ammonium hydroxide/87.5% ethyl acetate as eluent. Trituration of the product with ethyl acetate gave 45 mg (47%) as a white crystalline solid. Anal. for $C_{11}H_{23}NO_5S$ (MW 281.37): Calc'd.: C, 46.94; H, 8.24; N, 4.98. Found: C, 46.77; H, 8.16; N, 4.95.

Example 27

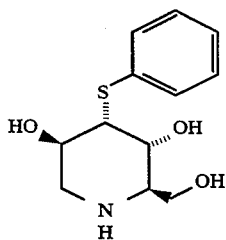

Preparation of 1,5-Dideoxy-1,5-imino-3-S-phenyl-3-thio-D-altritol

A solution of 100 mg (0.292 mmole) of the title compound 4 of Example 15 and 67 mg (0.35 mmole, 1.2 eqs) of p-toluenesulfonic acid monohydrate in 6 ml of ethanol was refluxed overnight. After cooling, the mixture was concentrated and then passed through a basic ion exchange column using 25% methanol/water as eluent. The appropriate fractions were washed with hexane, then concentrated to give the product as white solid. Anal. for $C_{12}H_{17}NO_2S \cdot \frac{1}{4} H_2O$ (MW 259.89): Calcd.: C, 55.47; H, 6.79; N, 5.39. Found: C, 55.08; H, 6.63; N, 5.25.

Example 28

Various illustrative compounds synthesized above were tested for inhibition of visna virus in vitro in a plaque reduction assay (Method A) or for inhibition of HIV-1 in a test which measured reduction of cytopathogenic effect in virus-infected syncytium-sensitive Leu-3a-positive CEM cells grown in tissue culture (Method B) as follows:

Method A

Cell and virus propagation

Sheep choroid plexus (SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at −70° C.

Plaque reduction assay

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5 ml of Medium 199 (M-199) supplemented with 2% lamb serum, 4 mM glutamine, 0.5% agarose and gentamycin was added to each well. Cultures were incubated at 37° C. in a humidified 5% $CO_2$ incubator for 3–4 weeks. To terminate the test, cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 well plate assay

The 96 well plate assay was performed similarly to the plaque assay above with modifications. SCP cells were seeded at $1 \times 10^4$ cells per well in 0.1 ml DME medium. When confluent, the wells were washed with serum free MEM and 25 μl of virus added in M-199 supplemented with 2% lamb serum. After 1 hour, 75 μL of medium containing test compound was added to each well containing virus. After 2–3 weeks incubation the cytopathic effect of the virus was determined by staining with a vital stain. Cell viability was measured by determining stain density using a 96 well plate reader.

Control wells without virus were completed to determine the toxicity of compounds.

Method B

Tissue culture plates were incubated at 37° C. in humidified, 5% $CO_2$ atmosphere and observed microscopically for toxicity and/or cytopathogenic effect (CPE). At 1 hour prior to infection each test article was prepared from the frozen stock, and a 20 μl volume of each dilution (prepared as a 10× concentration) was added to the appropriate wells of both infected and uninfected cells.

Assays were done in 96-well tissue culture plates. CEM cells were treated with polybrene at a concentration of 2 μg/ml, and an 80 μl volume of cells ($1 \times 10^4$ cells) was dispensed into each well. A 100 μl volume of each test article dilution (prepared as a 2× concentration) was added to 5 wells of cells, and the cells were incubated at 37° C. for 1 hour. A frozen culture of HIV-1, strain HTVL-III$_B$, was diluted in culture medium to a concentration of $5 \times 10^4$ TCID$_{50}$ per ml, and a 20 μl volume (containing $10^3$ TCID$_{50}$ of virus) was added to 3 of the wells for each test article concentration. This resulted in a multiplicity of infection of 0.1 for the HIV-1 infected samples. A 20 µl volume of normal culture medium was added to the remaining wells to allow evaluation of cytotoxicity. Each plate contained 6 wells of untreated, uninfected, cell control samples and 6 wells of untreated, infected, virus control samples.

On the 9th day post-infection, the cells in each well were resuspended and a 100 µl sample of each cell suspension was removed for use in an MTT assay. A 20 µl volume of a 5 mg/ml solution of 3-(4,5-dimethyl-thiazol-2-yl)-2,5-diphenyltetrazolium bromide (MTT) was added to each 100 µl cell suspension, and the cells were incubated at 37° C. in 5% $CO_2$ for 4 hours. During this incubation MTT is metabolically reduced by living cells, resulting in the production of a colored formazan product. A 100 µl volume of a solution of 10% sodium dodecyl sulfate in 0.01N hydrochloric acid was added to each sample, and the samples were incubated overnight. The absorbance at 590 nm was determined for each sample using a Molecular Devices $V_{max}$ microplate reader. This assay detects drug-induced suppression of viral CPE, as well as drug cytotoxicity, by measuring the generation of MTT-formazan by surviving cells.

Table 1, below, sets forth the results of the foregoing assays for visna virus inhibition and HIV inhibition by illustrative compounds prepared in the foregoing Examples.

TABLE 1

Anti-viral Activity of Sulfur-Analogs

| Example Compound No. | Visna Virus Inhibition | HIV Inhibition |
| --- | --- | --- |
| Ex. 8 Compnd. 3 | | $EC_{50}$ = 28.8 µg/ml |
| Ex. 12 | | $EC_{50}$ = 30.5 µg/ml |
| Ex. 13 | 83% @ 0.05 mM<br>76% @ 0.05 mM<br>65% @ 0.005 mM | |
| Ex. 15 Compnd. 1 | 59% @ 1.0 µM | |
| Ex. 15 Compnd. 3 | | 48% @ 10 µg/ml |
| Ex. 17 | 64% @ 1.0 mM | |
| Ex. 21 | | 30.4% @ 100 µg/ml |
| Ex. 23 | 51% @ 0.5 mM | |
| Ex. 27 | | 15.1% @ 100 µg/ml |

The compounds of Examples 10 and 17 also effectively inhibited glucosidase enzymes 20% and 64%, respectively, at 1 mM concentration as determined by conventional assays for these enzymes described in U.S. Pat. No. 4,973,602.

The antiviral agents described herein can be used for administration to a mammalian host infected with a virus, e.g. visna virus or in vitro to the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one mg/kg/day of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage from can be prepared by reference to general texts in the field such as, for example, *Remington's Pharmaceutical Sciences*, Ed. Srthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. A compound of the formula

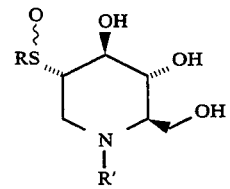

wherein
R=$C_1$-$C_4$ alkyl or phenyl
R'=H or butyl.

2. A compound of claim 1 in which R is methyl and R' is butyl.

* * * * *